United States Patent [19]
Hofmann

[11] Patent Number: 5,116,375
[45] Date of Patent: May 26, 1992

[54] KNEE PROSTHESIS

[76] Inventor: Aaron A. Hofmann, 1349 E. Princeton Ave., Salt Lake City, Utah 84105

[21] Appl. No.: 572,450

[22] Filed: Aug. 27, 1990

[51] Int. Cl.⁵ .............................................. A61F 2/38
[52] U.S. Cl. .................................................... 623/20
[58] Field of Search ............................ 623/16, 18, 20

[56] References Cited

U.S. PATENT DOCUMENTS
4,462,120  7/1984  Rambert .................. 623/20

FOREIGN PATENT DOCUMENTS
0103697  3/1984  European Pat. Off. ............. 623/20
0194326  9/1986  European Pat. Off. ............. 623/20

Primary Examiner—David Isabella
Attorney, Agent, or Firm—Kelly Bauersfeld & Lowry

[57] ABSTRACT

An improved knee joint prosthesis is provided of the type having a femoral component for attachment to the lower end of a patient's femur and an interengagable tibial component for attachment to the upper end of the patient's tibia. The tibial and femoral components are each formed from a high strength biocompatible material, with the tibial component typically supporting a meniscal bearing member of a high density plastic or the like for engaging the femoral component to accommodate natural or near-natural knee flexion. The bearing member includes an upwardly projecting stabilizing post having a posterior cam surface for engagement by a removably mounted stabilization rod extending between medial and lateral condyles of the femoral component. When used, the stabilization rod contacts the stabilization post during moderate to severe flexion of the knee prosthesis to extend the range of stable flexion of the prosthesis.

5 Claims, 2 Drawing Sheets

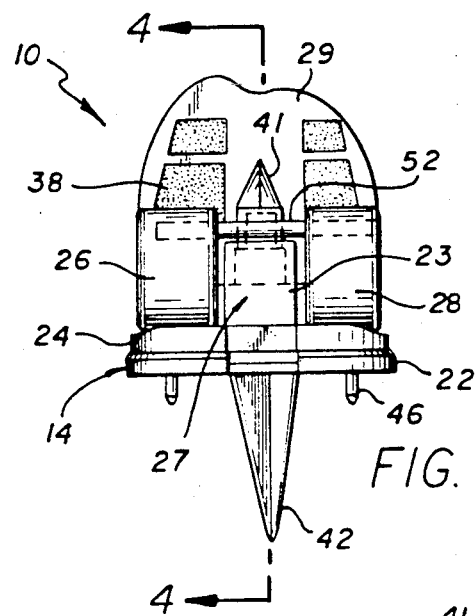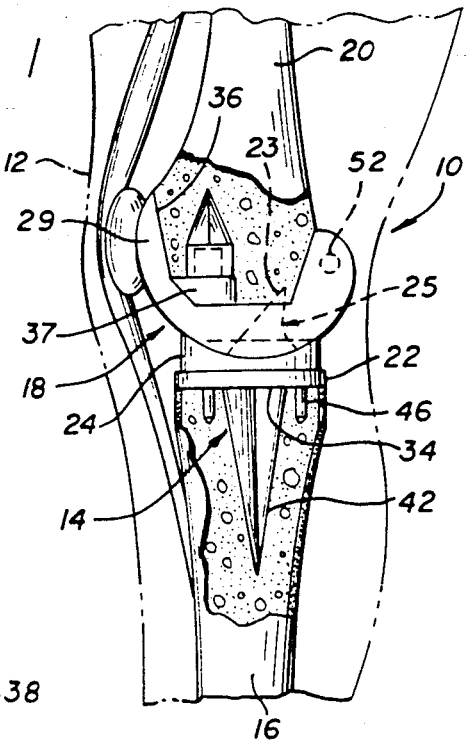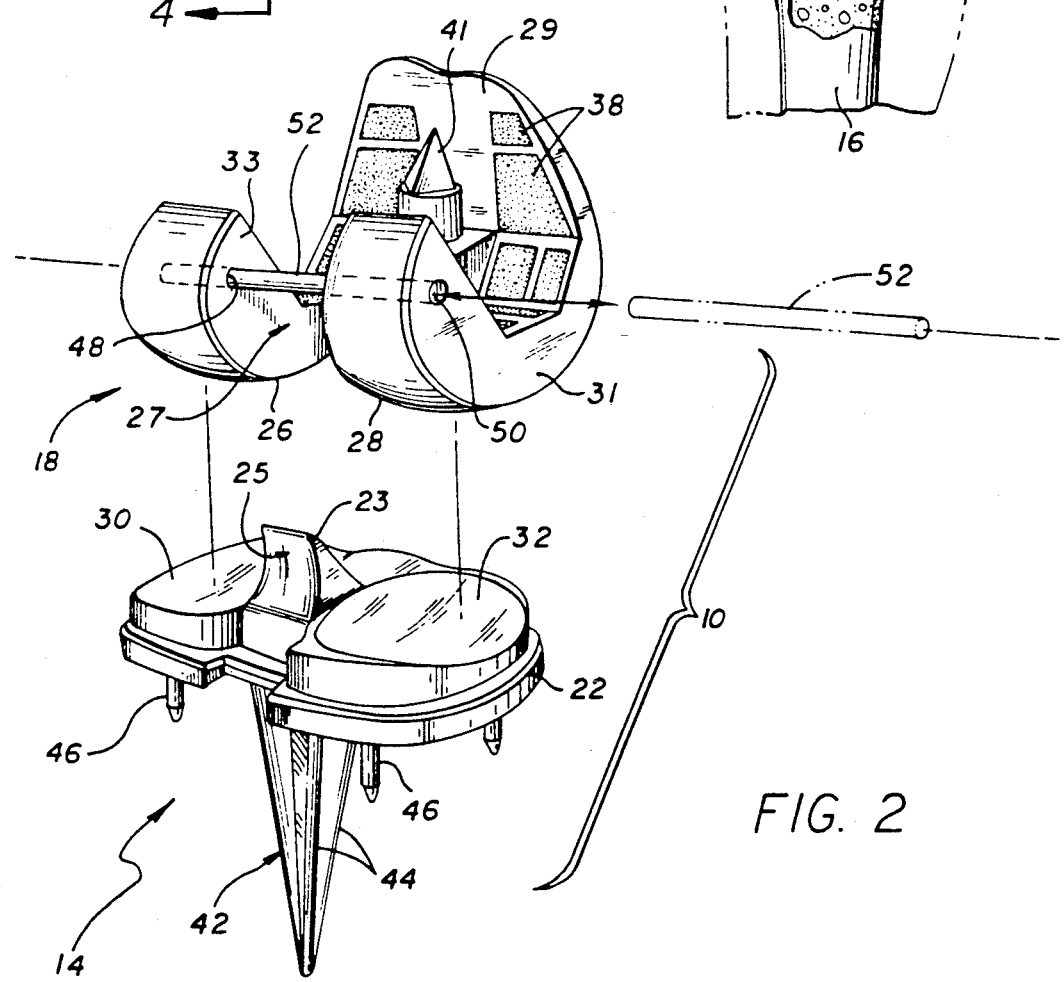

KNEE PROSTHESIS

BACKGROUND OF THE INVENTION

This invention relates generally to improvements in prosthetic devices used for reconstruction of the knee joint in humans. More particularly, this invention relates to an improved knee prosthesis, wherein the posterior stabilization of the prosthesis is enhanced during flexion movements, and further wherein flexibility is provided to the surgeon during the implantation as to the level of stabilization that is to be utilized.

Artificial or prosthetic joint mechanisms for implantation into animals, particularly humans, have been the subject of intensive research and development efforts for many years. Such prosthetic joint mechanisms have typically comprised one or more implant components formed from a relatively biostable material having selected structural properties and a unique shape to replace all or part of a selected anatomical joint, for example, a hip or knee joint. The implant components are installed by surgically accessing the joint and by resection of one or more bone surfaces to accommodate direct attachment thereto of the implant components. In the past, attachment of implant components to patient bone has been commonly achieved by use of bone cement, such as a methyl methacrylate-based cement or the like used as a grouting material to fill up the space between the receptive bone surface and the prosthetic component. More recently, however, a variety of structural and biological imcompatibility problems encountered with the use f bone cements have led to the development of so-called bone ingrowth materials. In such bone ingrowth materials, a surface coating of controlled porosity is provided on a prosthesis component in a position for intimately contacting patient bone to achieve a significant degree of postoperative bone and/or tissue ingrowth, and thereby obtain a mechanical interlock with patient bone without utilizing bone cement.

The human knee joint has presented particularly difficult problems in the development of a satisfactory prosthetic joint. More specifically, the human knee joint is recognized as an extremely complex mechanical structure which is subjected to high mechanical loads of widely varying magnitude and direction during normal function. Unfortunately, the knee joint is also subject to a relatively high frequency of disabling injury occurrence since the knee joint bears full body weight and can be exposed to twisting forces and blows from all directions. The greatest risk lies in sports that include pivoting, twisting, running, and jumping, such as tennis, basketball, skiing and racquetball, and, of course, contact sports such as soccer and football.

As a result, a wide variety of knee prostheses have been proposed in the prior art, typically to include matingly configured femoral and tibial components adapted respectively for implantation onto the lower end of a resected femur and the upper end of a resected tibia, with appropriate plastic meniscal bearing components interposed therebetween. In the majority of these prior art knee prostheses, the general configuration of the femoral and tibial components has resembled the general physiology of the natural knee joint, namely, to include medial and lateral condyles on the femoral component which are supported by the meniscal bearing components on the tibial component. Desirably, the prosthesis components are retained in bearing engagement throughout a range of knee flexion by the natural connective tissues including the ligament and tendon structure of the knee joint.

In some cases involving significant damage or injury to the connective tissues in addition to the bone structure, it is necessary or desirable to utilize a special prosthesis device having posterior stabilization features to prevent dislocation of the prosthetic components during moderate to severe knee flexion. That is, depending upon the condition of the connective tissues, the wide range of natural knee flexion can create a significant risk of dislocation when substantial flexion angles are encountered. To address this problem, specialized prostheses having structural components designed to prevent posterior dislocation have been developed, as described, for example, in U.S. Pat. No. 4,298,992. However, since the need for posterior stabilization in a particular patient often cannot be determined until the time of surgery, it has been necessary for the surgeon to speculate regarding the patient's need for posterior stabilization or otherwise have more than one prosthesis available in the operating room for selection in the course of the implantation surgery.

There exists, therefore, a significant need for an improved knee prosthesis which can be adapted quickly and easily at the time of implantation surgery to provide posterior stabilization in accordance with patient need. The present invention fulfills these needs and provides further related advantages.

SUMMARY OF THE INVENTION

In accordance with the invention, an improved knee prosthesis includes a femoral component for attachment to the lower end of a patient's femur and an interengagable tibial component for attachment to the upper end of the patient's tibia. The tibial and femoral components are each formed from a high strength biocompatible material, with the tibial component supporting a meniscal bearing member of a high density plastic or the like for rotatably and slidably supporting the femoral component to accommodate natural or near-natural knee flexion.

The tibial and femoral components each include a base surface presented in a direction toward the associated tibia or femur for attachment thereto. During implantation surgery, the tibia and femur are surgically resected to expose cancellous bone and to matingly receive the tibial and femoral components, respectively. In a preferred form, the attachment of the tibial and femoral components to the patient bone is achieved by a combination of mechanically interlocking pins and/or the use of porous bone ingrowth surfaces.

In accordance with the invention, the meniscal bearing member includes an upwardly projecting stabilizing post having a cam surface on the posterior surface thereof. This stabilizing post projects upwardly from the tibial component into a rearwardly open intercondylar recess defined between the medial and lateral condyles of the femoral component. A stabilization rod is provided for optional mounting onto the femoral component to bridge and close the otherwise open rear end of the intercondylar recess, in a position to engage the posterior cam surface during moderate to severe knee flexion. Such cam surface engagement effectively stabilizes the prosthesis to minimize posterior dislocation risk in some patients. Alternately, the stabilization rod may be omitted during implantation surgery, depending upon the condition of the patient's knee and supporting structure, thereby permitting the surgeon to variably select the degree of posterior stabilization as needed for a specific patient.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a side elevation view, partially in vertical section, illustrating a knee prosthesis embodying the novel features of the present invention and implanted within the knee of a patient;

FIG. 2 is an exploded perspective view of the knee prosthesis;

FIG. 3 is a posterior elevation view of the knee prosthesis;

DETAILED DESCRIPTION OF THE PREFERRED EMBODIMENT

Figure 4:
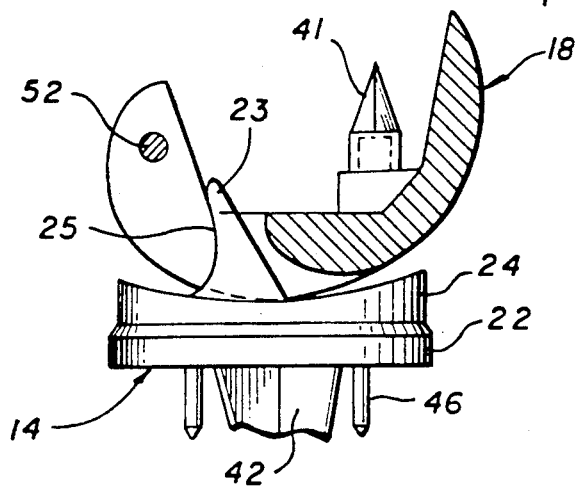
FIG. 4 is an anterior-posterior vertical section taken generally on the line 4—4 of FIG. 3, and showing the knee prosthesis with the leg in full extension.

As shown in the exemplary drawings, a knee prosthesis referred to generally by the reference numeral 10 is provided for implantation into the knee 12 of a patient, as viewed in FIG. 1. The knee prosthesis 10 includes a tibial component 14 adapted for secure and stable fixation onto the upper end of a patient's resected tibia 16, and a femoral component 18 adapted for secure and stable fixation onto the lower end of a patient's resected femur 20. The tibial component 14 and femoral component 18 are interengagable and are designed as a prosthetic replacement for the knee so as to accommodate natural or near-natural flexion of the knee joint. These tibial and femoral components 14 and 18 are constructed generally from known biocompatible surgical implant materials, such as cobalt chrome or titanium alloys, stainless steel, composites, or other surgical implant materials known to those skilled in the art.

The tibial component 14 traditionally provides an upper plateau or tray 22 defining a load-bearing structure which commonly supports a meniscal bearing member 24 of a high density plastic material, such as polyethylene or the like, selected for relatively low friction engagement by the femoral component 18. The femoral component 18 is commonly shaped to provide downwardly presented medial and lateral condyles 26 and 28 simulating the pre-surgical geometry of the femoral condyles and shaped for seated engagement within generally mating medial and lateral recesses 30 and 32 in the bearing member 24. An upwardly projecting stabilizing post 23 having a curved posterior cam surface 25 is provided between the medial and lateral recesses 30 and 32 in the bearing member 24, wherein this post 23 is desirably formed integrally with the bearing member 24.

The relative geometries of the condyles 26 and 28 and the bearing member recesses 30 and 32 are selected to accommodate natural or near-natural articulatory knee motion under natural muscle and ligament control. Thus, the meniscal bearing member 24 is tapered from the medial recess 30 to the lateral recess 32 such that the lateral recess 32 is typically smaller than the medial recess 30. An intercondylar recess 27 is provided between the upwardly projecting posterior walls 31 and 33 of the lateral condyle 26 and medial condyle 28, respectively. An upwardly projecting front or patellar wall 29 interconnects the front end of the condyles, such that the recess 27 is rearwardly open. The specific geometries of these surfaces and the specific manner of supporting or fixating the bearing member 24 on the tibial component 14 are generally known in the art and thus are not described in further detail herein.

The tibial and femoral components 14 and 18 of the improved knee prosthesis 10 are implanted generally in accordance with known surgical techniques. More particularly, the subject knee joint of the patient is surgically accessed and the cortical bone defining the condyles of the tibia 16 and femur 20 at the knee joint is resected to expose underlying cancellous bone. Importantly, this surgical resection tailors the geometry of the tibia 16 and femur 20 to accommodate substantially mating flush seated engagement of the patient bone with the base surfaces 34 and 36 of the tibial and femoral components 14 and 18, respectively.

The base surface 36 of the femoral component 18 comprises an extended surface area for contacting the surgically exposed cancellous bone of the femur 20. In the preferred form, this extended surface area includes one or more attachment zones 38 defined by a selected surface substance or ingrowth material having a controlled porosity size and density for accommodating secure and stable post-surgical biological ingrowth of cancellous bone and/or localized tissue. The particular porous ingrowth material may vary, with examples of such materials comprising coatings of small spherical beads or fibers or other porous substances of a biologically compatible material, such as titanium or cobalt chrome, thermoplastic, plasma sprays, and/or composite materials, such as blended hydroxy apatites and fibrous materials, and others. The femoral component base surface 36 may further include a shelf 37 immediately behind the patellar wall 29 from which a mounting post 41 extends upwardly for mechanically interlocking with the patient's femur. This fixation post 41 may also be coated or otherwise include zones coated with the same ingrowth material, if desired.

The base surface 34 of the tibial component 14 normally includes a central tapered anchoring or fixation post 42 which extends into the tibia 16 and may include a plurality of antirotation flutes 44. Each corner of the tibial component base surface 34 may also include a short projecting anchoring pin 46 which interlocks with the patient's tibia. The base surface 34 may further include a plurality of porous attachment zones (not shown), similar to the zones 38 of the femoral component 18. The anchoring post 42 and the anchoring pins 46 may also be coated with ingrowth material. The anchoring post 42 and pins 46 provide extensive surface areas presented anteriorly and posteriorly to enhance resistance to rotation while widely distributing rotational forces in a manner avoiding stress concentrations potentially detrimental to ingrowth interdigitation.

The posterior walls 31 and 33 of the medial and lateral condyles 26 and 28 include aligned horizontal holes 48 and 50 respectively. The hole 48 extends completely through the posterior wall 31 of the medial condyle 26, whereas the hole 50 in the posterior wall 33 of the lateral condyle 28 may extend only partially therethrough from the intercondylar recess 27. A posterior stabilizing rod 52 is adapted to be inserted through the hole 48 in the posterior wall 31 of the medial condyle 26, bridging the rearward extent of the intercondylar recess 27, and into the hole 50 in the posterior wall 33 of the lateral condyle 28.

The knee prosthesis 10 is shown in FIG. 4 in a generally stable position with the patient's leg fully extended, such that the medial and lateral condyles 26 and 28 nest on the medial and lateral recesses 30 and 32, respectively, of the meniscal bearing member 24. At this point, the stabilizing rod 52 is disposed above and behind the cam surface 25 of the stabilizing post 23 in spaced relation therewith. Under minimal to moderate degrees of flexion of the leg, the stabilizing rod 52 and cam surface 25 continue to remain in spaced relation and are thus functionally dormant as the condyles 26 and 28 roll and slide within the bearing recesses 30 and 32.

Figure 5:
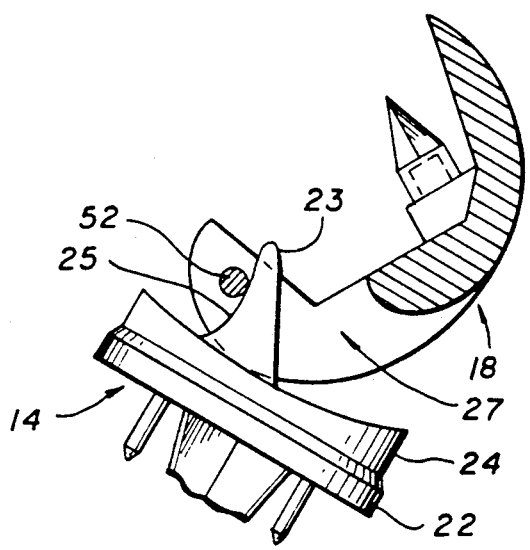
FIG. 5 and 6 are anterior-posterior vertical sections similar to FIG. 4, but depicting the knee prosthesis with the leg in progressively increased flexion.
Figure 6:
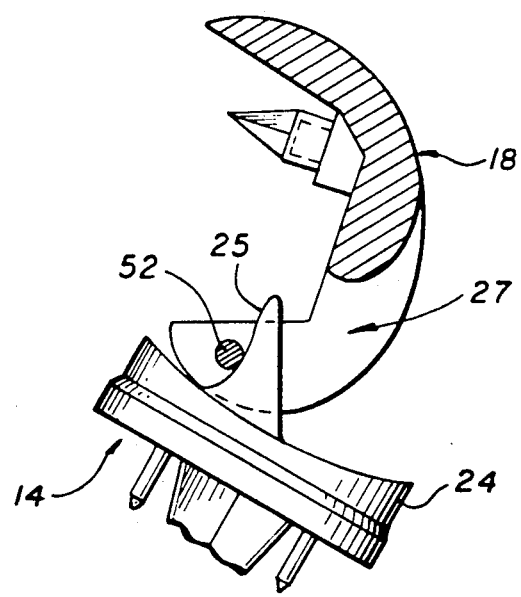

As leg flexion increases further, the relative positions of the tibial and femoral components displaces the stabilizing rod 52 into engagement with the posterior cam surface 25 of the stabilizing post 23 (FIG. 5). Further leg flexion beyond this point forces the femoral condyles 26 and 28 to roll and slide within (FIG. 5) the bearing recesses 30 and 32 such that the axis of joint flexion shifts posteriorly. This shift in combination with the contour of the cam surface 25 permits a high degree of leg flexion to occur without interference between the posterior extremity of the femur and the posterior extremity of the tibial component, such that risk of prosthesis dislocation is minimized or eliminated. That is, the stabilizing rod 52 and cam surface 25 serve to stabilize the function of the prosthesis 10 at moderate to full flexion and thus control the relative anterior-posterior position of the femur with respect to the tibia.

Figure 7:
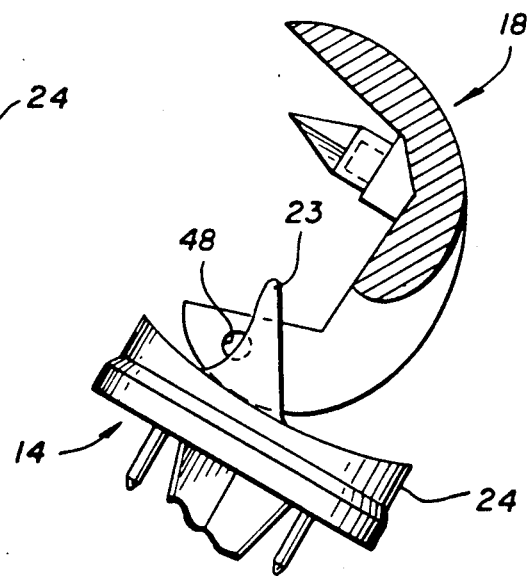
FIG. 7 is an anterior-posterior vertical section similar to FIG. 4, but depicting the knee prosthesis without the posterior stabilization rod and the leg at substantially full flexion.

Since the exact condition of the patient's knee and the extent of deterioration thereof cannot always be determined precisely before surgery, the present invention beneficially permits the surgeon to determine the need for posterior prosthesis stabilization during the surgical procedure and to react accordingly by installing or omitting the rod 52. More specifically, the extent of injury or damage to the various ligaments and/or tendons at the knee joint may dictate a need for posterior stabilization of the knee prosthesis. When such stabilization is indicated, the surgeon can install the stabilizing rod 52 during surgery by press-fit insertion through the holes 48 and 50 in the posterior walls 31 and 33 of the medial and lateral condyles 26 and 28. Conversely, if the overall condition of the supporting structure of the patient's knee contraindicates a need for posterior stabilization, then the stabilizing rod 52 can be omitted from the prosthesis (FIG. 7). In either case, the same basic femoral component 18 is utilized.

While the attachment of the tibial and femoral components 14 and 18 has been described in detail utilizing the technique of bone ingrowth material, it should be recognized that cemented fixation of the prosthetic knee of the present invention is also possible and in some circumstances may be desirable or necessary.

A wide variety of modifications and improvements to the knee prosthesis described herein are believed to be apparent to those skilled in the art. Accordingly, no limitation on the present invention is intended by way of the description herein, except as set forth in the appended claims.

What is claimed is:

1. A knee joint prosthesis, comprising:
   a femoral component for fixation to the resected end of a patient's femur, said femoral component including spaced medial and lateral condyles defining a rearwardly open intercondylar recess therebetween, and a patellar wall anteriorly interconnecting said medial and lateral condyles;
   a tibial component for fixation to the resected end of a patient's tibia;
   meniscal bearing means on said tibial component for supporting said medial and lateral condyles of said femoral component; and further
   a stabilizing post having a posterior facing cam surface formed thereon, said stabilizing post projecting upwardly from said tibial component at a position between said medial and lateral condyles; and
   stabilization mean for removable mounting onto said femoral component to substantially bridge between said medial and lateral condyles to close the rear end of said intercondylar recess, said stabilization means engaging said cam surface upon moderate to severe joint flexion to stabilize the relative position of said femoral and tibial components.

2. The knee joint prosthesis of claim 1 wherein said medial and lateral condyles respectively define spaced medial and lateral posterior walls having aligned holes formed therein, said stabilization means comprising a removable stabilization rod for insertion into said holes to bridge said intercondylar recess.

3. The knee joint prosthesis of claim 2 wherein said meniscal bearing means defines medial and lateral recesses for respectively supporting said medial and lateral condyles, said stabilizing post projecting upwardly between said medial and lateral recesses.

4. The knee joint prosthesis of claim 3 wherein said stabilizing post is formed integrally with said bearing means.

5. A knee joint prosthesis, comprising:
   a femoral component for attachment to the lower end of a patient's femur;
   a tibial component for attachment to the upper end of a patient's tibia, said femoral and tibial components having engaging articulatory surfaces for accommodating substantially normal patient knee joint motion; and
   stabilization means operably associated with said femoral and tibial components to selectively posteriorly stabilize the knee joint prosthesis during moderate to severe knee flexion, said stabilization means including an upwardly projecting stabilizing post on said tibial component and having a posterior facing cam surface formed thereon, and a stabilization rod removably mounted on said femoral component to engage said cam surface during moderate to severe knee flexion.

* * * * *